(12) United States Patent  
Takada (10) Patent No.: US 6,695,771 B2  
(45) Date of Patent: Feb. 24, 2004

(54) SELF-PROPELLED COLONOSCOPE

(76) Inventor: Masazumi Takada, 622-26 Takatsukashinden, Matsudo-city, Chiba, 270-2222 (JP)

( * ) Notice: Subject to any disclaimer, the term of this patent is extended or adjusted under 35 U.S.C. 154(b) by 0 days.

(21) Appl. No.: 10/108,630

(22) Filed: Mar. 29, 2002

(65) Prior Publication Data

US 2003/0088152 A1 May 8, 2003

(30) Foreign Application Priority Data

Nov. 6, 2001 (JP) ........................................ 2001-340568

(51) Int. Cl.[7] ................................................. A61B 1/12
(52) U.S. Cl. ..................... 600/114; 600/434; 604/95.01; 604/95.03
(58) Field of Search ................................. 600/101, 139, 600/146, 147, 148, 149, 114, 434, 585; 604/95.01, 95.03, 164.13

(56) References Cited

U.S. PATENT DOCUMENTS

| | | | | |
|---|---|---|---|---|
| 4,561,427 A | * | 12/1985 | Takada | 600/114 |
| 5,562,601 A | * | 10/1996 | Takada | 600/114 |
| 6,071,234 A | * | 6/2000 | Takada | 600/114 |
| 6,162,171 A | * | 12/2000 | Ng et al. | 600/141 |
| 6,224,544 B1 | | 5/2001 | Takada | |
| 6,461,295 B2 | * | 10/2002 | Takada | 600/155 |
| 6,537,206 B2 | * | 3/2003 | Takada | 600/114 |

FOREIGN PATENT DOCUMENTS

JP 2000-135199 5/2000

\* cited by examiner

*Primary Examiner*—John Mulcahy  
*Assistant Examiner*—Kenneth G. Sehopfer  
(74) *Attorney, Agent, or Firm*—Young & Thompson

(57) ABSTRACT

The self-propelled colonoscope (1) is self-inserted into a colon by driving endless belts (17) mounted on the outside of the bending section (15) of the insertion tube (9). The cross section of the endless belt (17) is substantially circular and a rack gear teeth having a circular cross section are formed on the outside of the endless belts (17). A recess having a circular cross section and pinion gear teeth which correspond to the shape of the endless belt and the rack gear teeth. Since the endless belt (17) has a circular cross section, it can easily bend in all radial directions. Upon insertion of the insertion tube (9) into the colon, the endless belt (17) can easily follow the movement of the insertion tube (9).

2 Claims, 7 Drawing Sheets

SELF-PROPELLED COLONOSCOPE

FIELD OF THE INVENTION

The present invention relates to a self-propelled colonoscope, which does not cause pain to a patient during a colonoscopic examination of the colon.

PRIOR ART

Colonoscopic examination is currently carried out by inserting a colonoscope by hand, such that the examination may cause pain to a patient by excessively extending or bending the colon.

Figure 7:
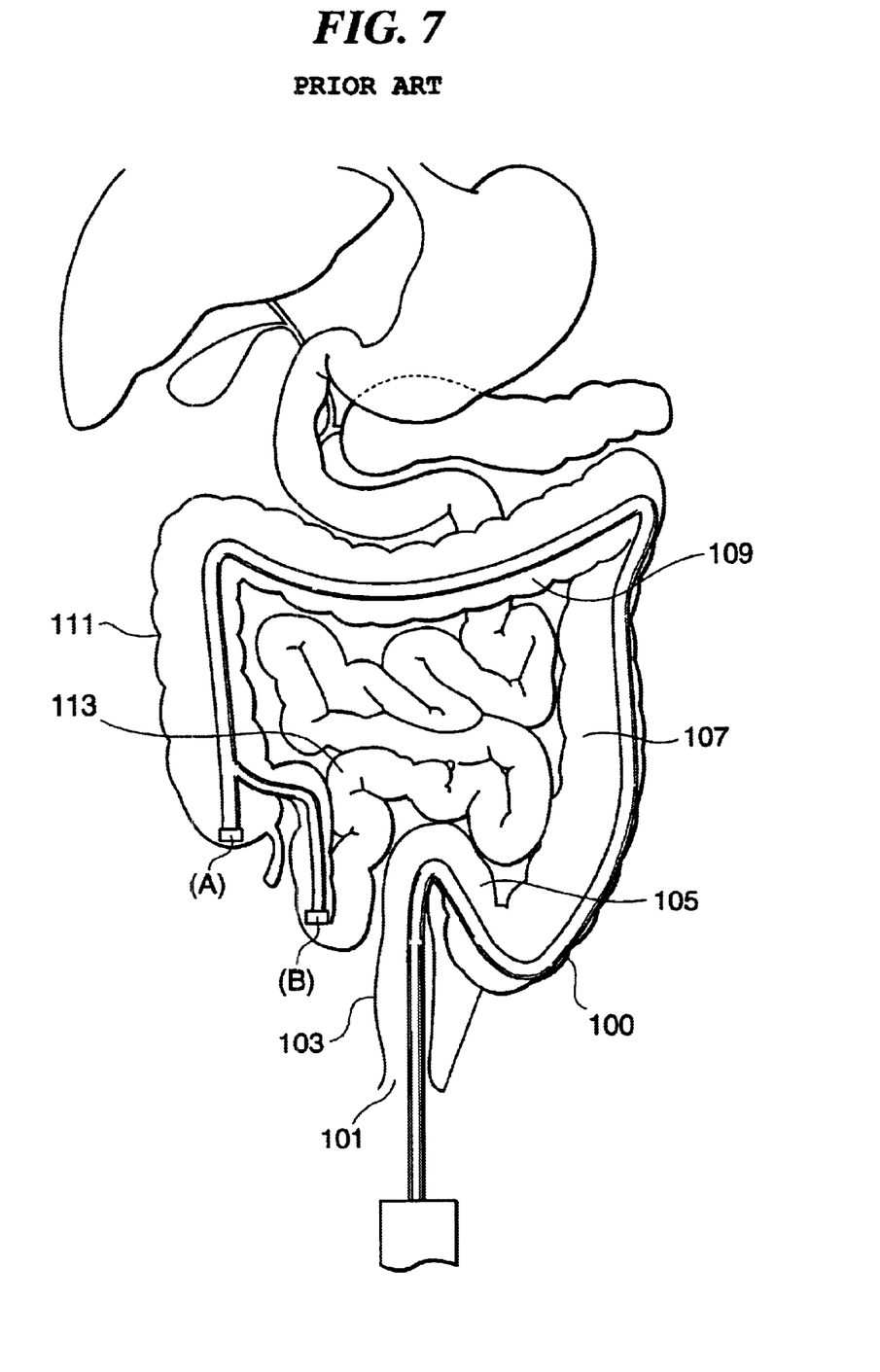
FIG. 7 is a drawing schematically showing an insertion path of a conventional colonoscope.

FIG. 7 is a drawing schematically showing an insertion path of a conventional colonoscope.

The tip of the insertion tube 100 of the colonoscope is inserted from the anus 101 into the colon 103 and advances from the sigmoid colon 105 to the ileum 113, by passing through the descending colon 107, a transverse colon 109 and an ascending colon 111. The tip of the insertion tube 100 may be inserted until it reaches the distal end of the colon (A) or it may be inserted into the ileum 113 for about 25 cm (B).

As shown in FIG. 7, since the sigmoid colon 105, positioned near the insertion point of the colonoscope, is sharply bent and has an S-shape, considerable operator skill is necessary to pass the insertion tube 100 through this portion. Further, the procedure causes increased pain to the patient.

Accordingly, in order to reduce the pain to the patient, in Patent Application Number Hei. 11-99600, the inventor of the present invention has proposed a colonoscope self-propelled along the colon. The colonoscope can be self-inserted into the colon by driving endless belts arranged on the outside of the flexible section of the insertion tube.

In such colonoscope, the endless belts are driven and contact the outside thereof with a wall of the colon to introduce the tip of the colonoscope into the colon by friction between the colon wall and the endless belts.

SUMMARY OF THE INVENTION

An object of the invention is therefore to provide a self-propelled colonoscope having improved bending ability of the insertion tube and self-propelling ability.

According to an aspect of the present invention, a colonoscope which can be self-inserted into a colon by driving an endless belt arranged on the outside of a flexible section of an insertion tube is provided, wherein a cross section of said endless belt is substantially circular, rack gear teeth having a circular cross section are formed on the outside of the endless belt, and a recess having a semi-circular cross section and pinion gear teeth which correspond to the shapes of the endless belt and the rack gear teeth are formed on the outside of a pulley for driving the endless belt.

The endless belt has a vertical circular cross section with respect to the longitudinal axis so as to have constant flexibility in all radial directions to the axis, thereby flexibly bending in all radial directions. Thus, when the insertion tube is inserted along the bending of the sigmoid colon, the endless belt can easily follow the movement of the insertion tube.

Since the rack gear teeth are formed on the outside of the endless belt, a large friction force develops between the outside of the endless belt and the wall of the colon such that the self-propelling ability of the colonoscope is improved.

Moreover, since the rack gear teeth are formed on the outside surface of the endless belt, if the endless belt should twist during operation, a part of the endless belt will contact and rub against the wall of the colon. Further, the pinion gear teeth and the recess formed on the outside of the pulley drive the endless belt such that the pulley is engaged with the endless belt tightly to increase the driving force of the endless belt.

Generally, the diameter of the insertion tube of a colonoscope conventionally used is 11.3 to 14.2 mm. When the tip of the colonoscope advances into the colon, the inner ring length and the outer ring length of the inserted insertion tube differ due to the bending of the colon. In the present invention, the length of the endless belt is 102 to 104% of a length such endless belt would have if it were tensely held around the inside and the outside of the insertion tube in the longitudinal direction while the insertion tube is kept straight. Thus the length of the insertion tube has an allowance corresponding to the difference between the lengths of the inner ring and the outer ring of the inserted insertion tube. Accordingly, the endless belt can follow the bending of the insertion tube and enables the colonoscope to advance into the colon stably. At this time, the endless belt and the pulley are tightly engaged and can not be disengaged regardless of any allowance of the endless belt. Further, the outside surface of the endless belt and the outside surface of the pulley may be coated with high frictional material so that the rack gear teeth and the pinion gear teeth will be engaged tightly thereby preventing the endless belt from running idle.

In the present invention, the outside surface of the endless belt may be coated with high frictional material. Thus, the friction force between the endless belt and the wall of the colon will be increased thereby improving the self-propelling ability.

DESCRIPTION OF THE PREFERRED EMBODIMENT

Referring to the attached drawings, details of the embodiments of the present invention will be set forth.

Figure 1:
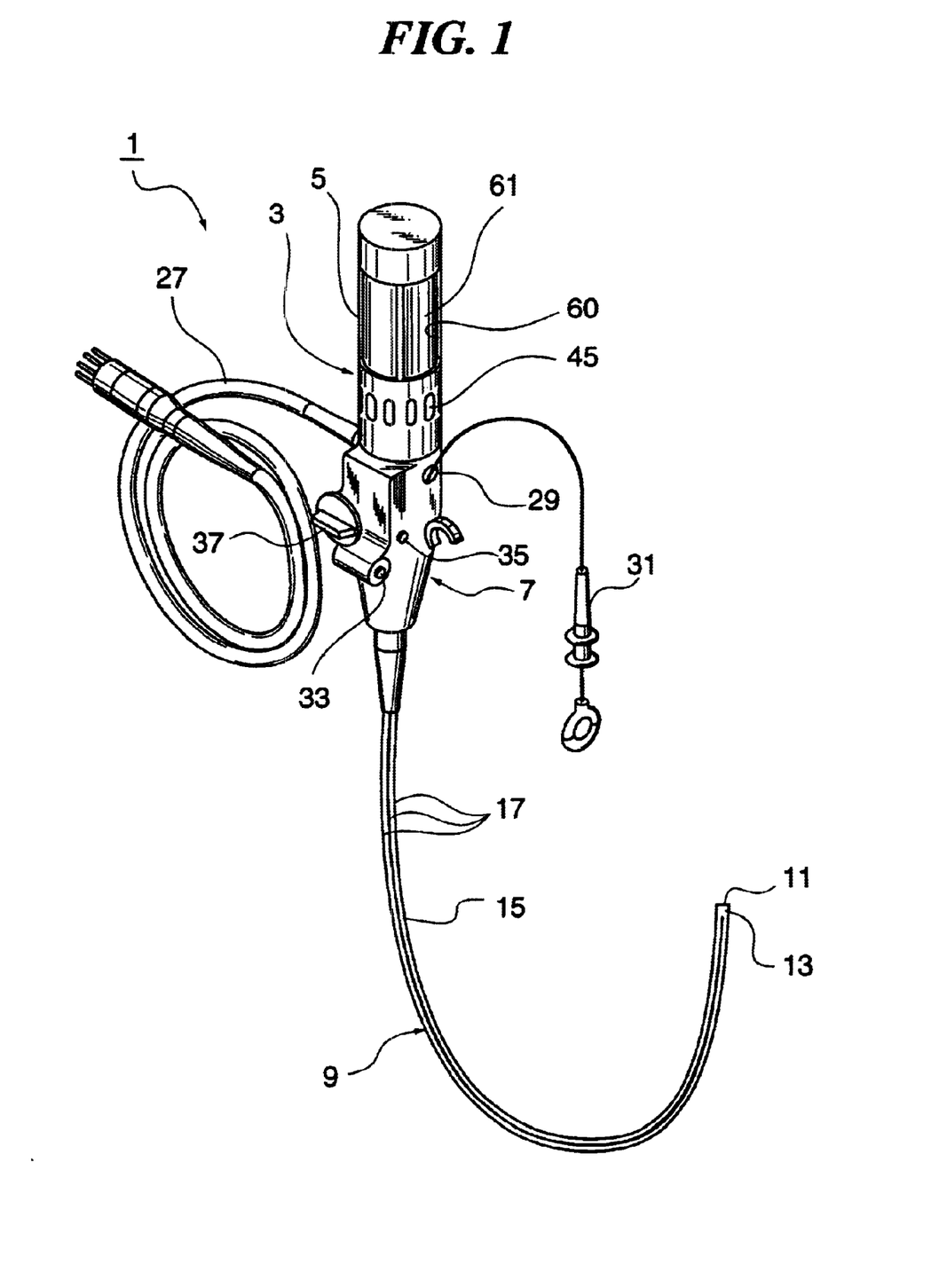
FIG. 1 is a drawing showing a perspective view of the self-propelled colonoscope according to one embodiment of the present invention.

FIG. 1 is a drawing showing a perspective view of the self-propelled colonoscope according to one embodiment of the present invention.

A self-propelled colonoscope 1 is provided with a belt driving unit 5 covered with a driving unit casing 3 at its upper part, an operation unit 7 under the belt driving unit, and an insertion tube 9 extending from the operation unit 7. The insertion tube 9 comprises a distal section 11, a bending section 13, and a flexible section 15. A plurality of endless belts 17 are longitudinally arranged on a surface of the flexible section 15.

Figure 2:
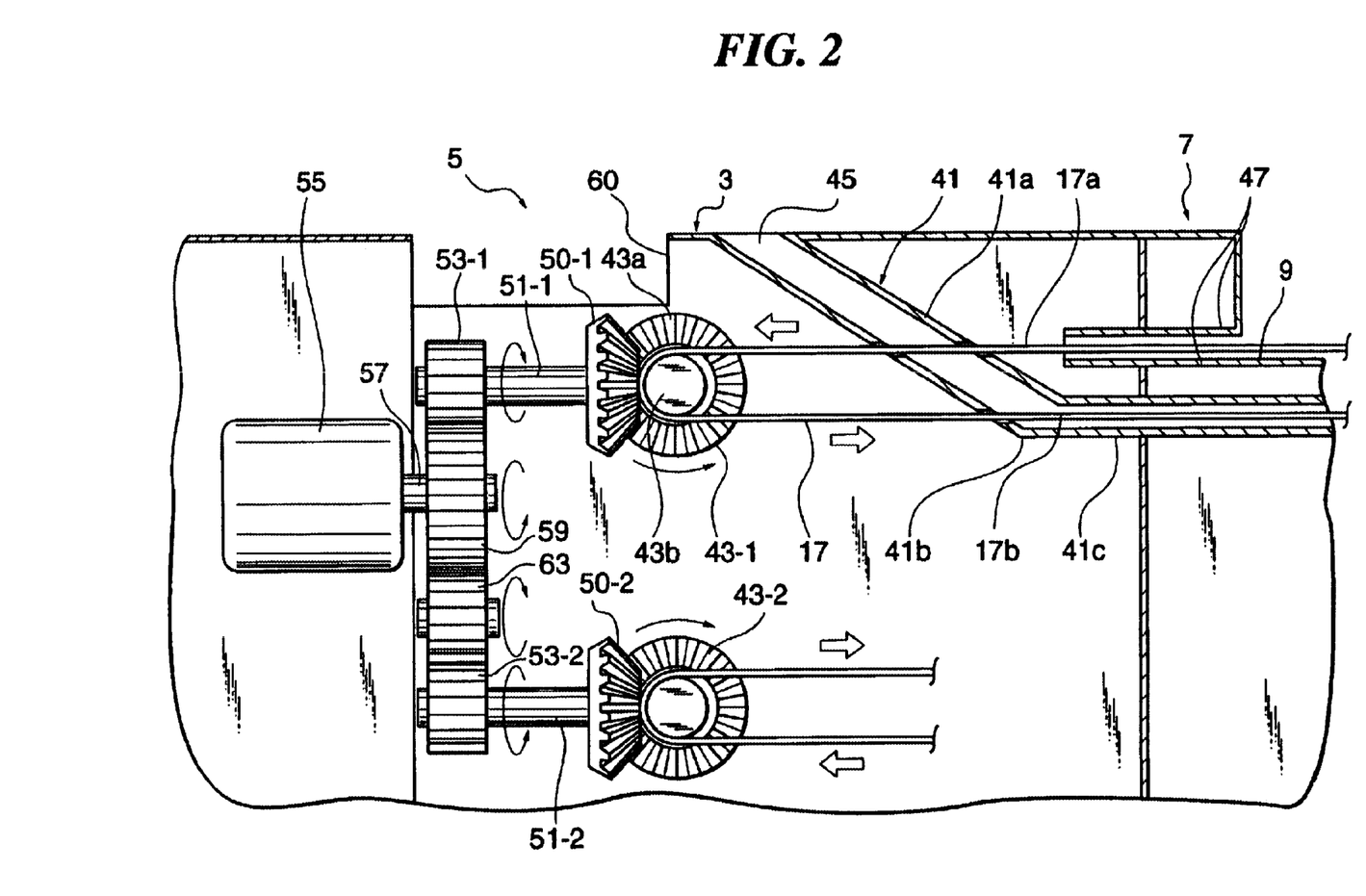
FIG. 2 is a drawing schematically showing a side sectional view of the driving unit of the colonoscope according to the invention.

FIG. 2 is a drawing schematically showing a side sectional view of the driving unit of the colonoscope according to the invention.

Figure 3A:
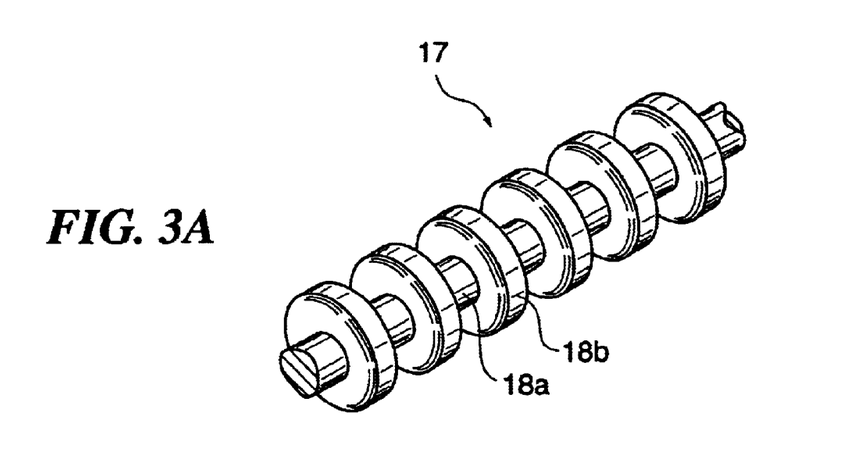
FIG. 3(A) is a drawing schematically showing a perspective view of the structure of the endless belt of the colonoscope according to the present invention.
Figure 3B:
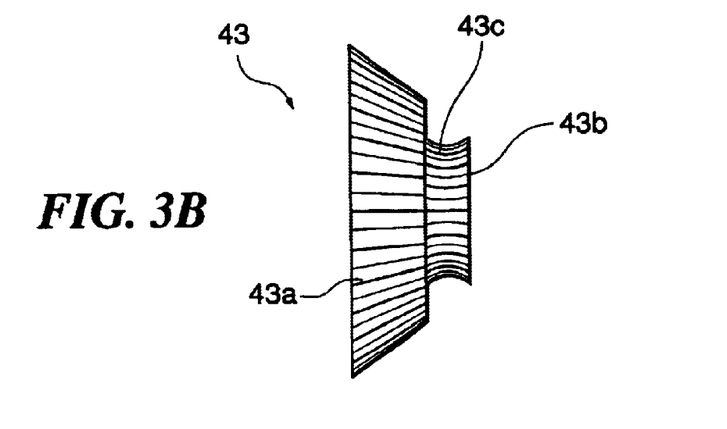
FIG. 3(B) is a drawing schematically showing a perspective view of the pulley on which the endless belts are wound.
Figure 3C:
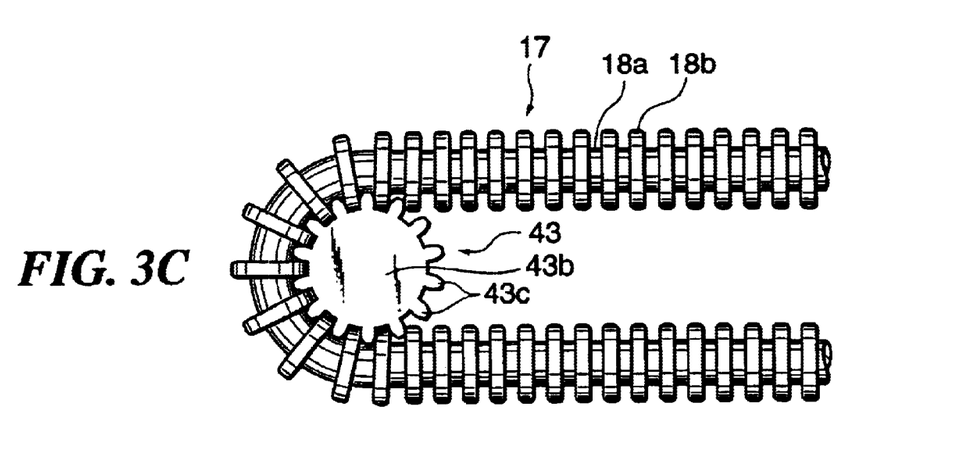
FIG. 3(C) is a drawing schematically showing a sectional view of engagement state between the endless belt and the pulley.

FIG. 3(A) is a drawing schematically showing a perspective view of the structure of the endless belt of the colonoscope according to the present invention, FIG. 3(B) is a drawing schematically showing a perspective view of the pulley on which the endless belts are wound, and FIG. 3(C) is a drawing schematically showing a sectional view of engagement state between the endless belt and the pulley.

Figure 4:
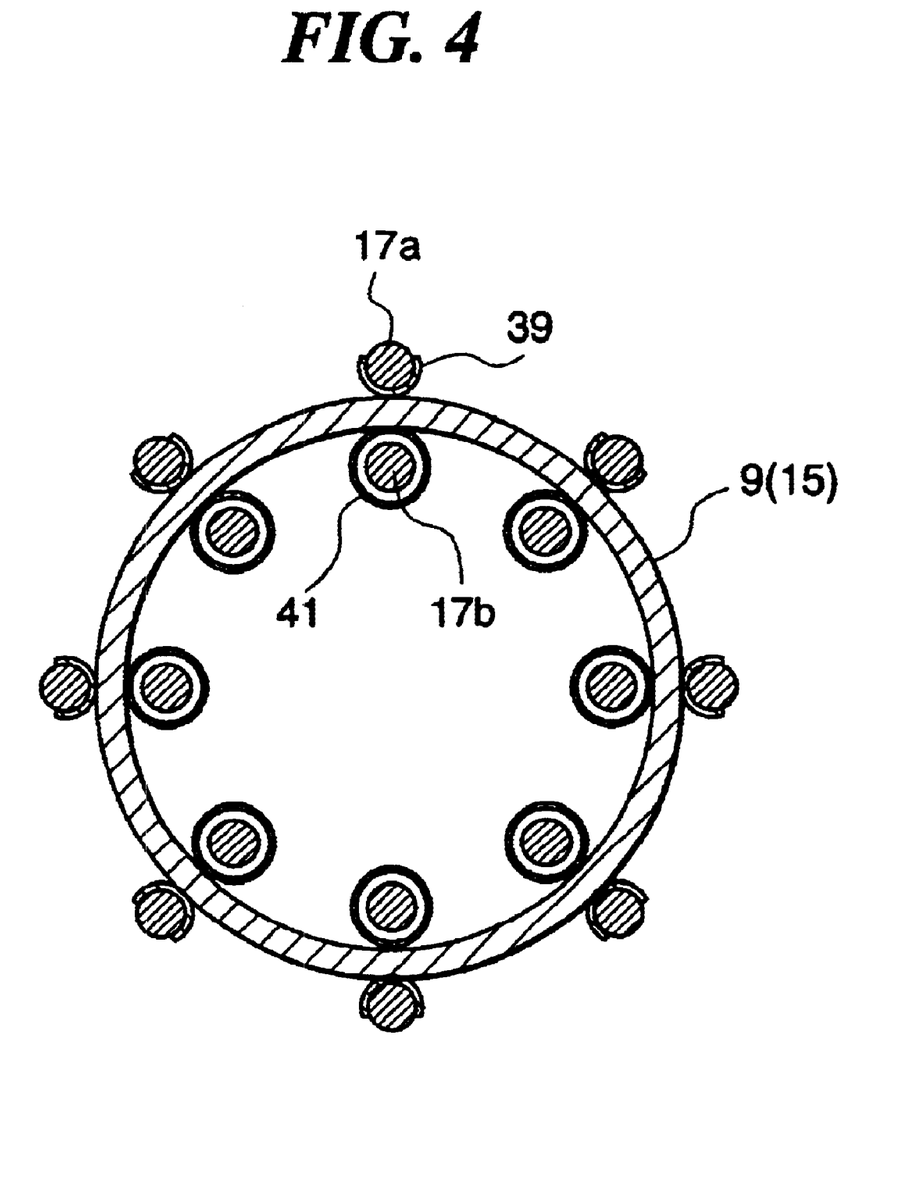
FIG. 4 is a drawing schematically showing a sectional view of the flexible section of the insertion tube of the colonoscope according to the invention.

FIG. 4 is a drawing schematically showing a sectional view of the flexible section of the insertion tube of the colonoscope according to the invention.

Figure 5:
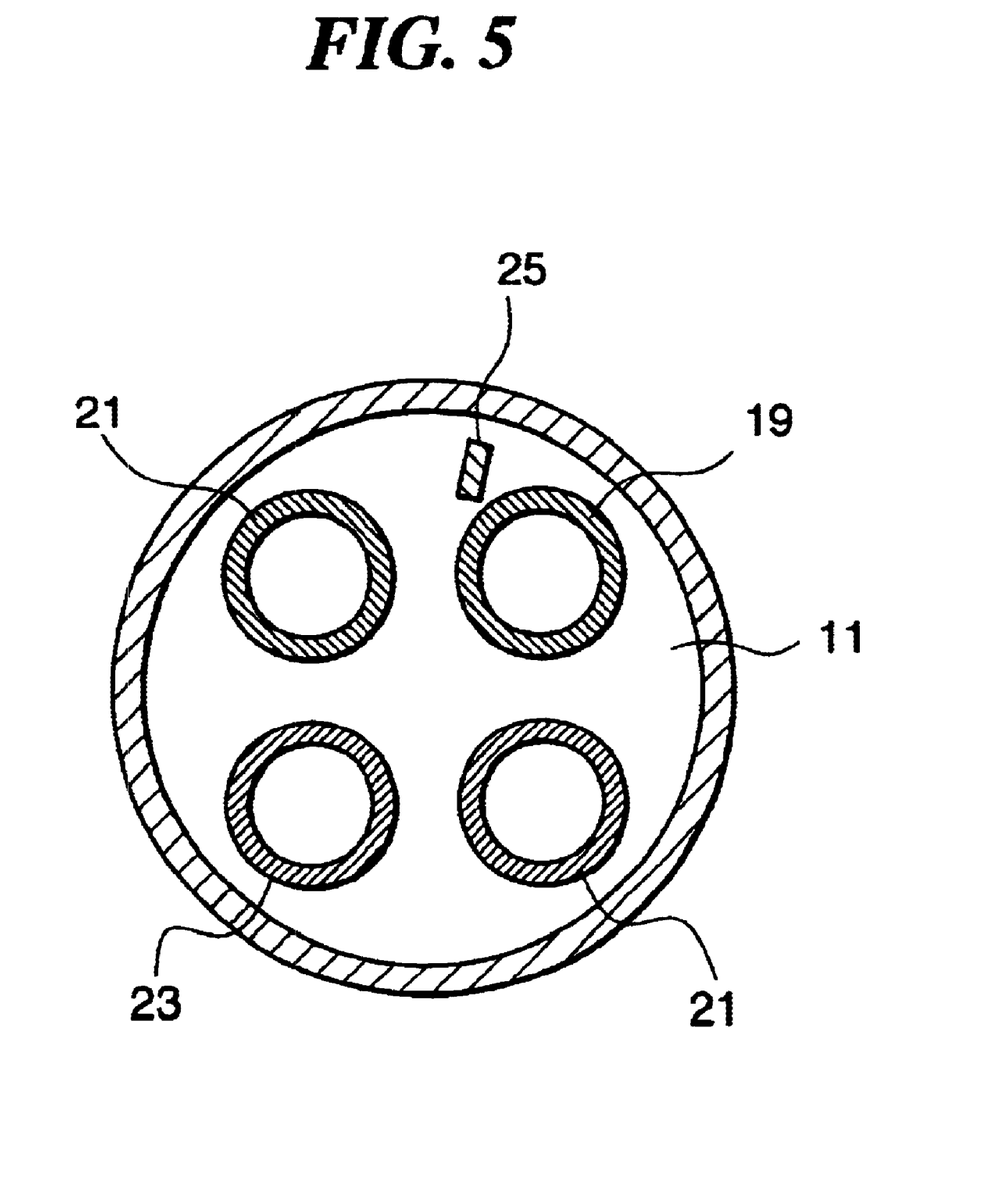
FIG. 5 is a drawing showing a front view of the distal section of the insertion tube of the colonoscope according to the invention.

FIG. 5 is a drawing showing a front view of the distal section of the insertion tube of the colonoscope according to the invention.

Figure 6:
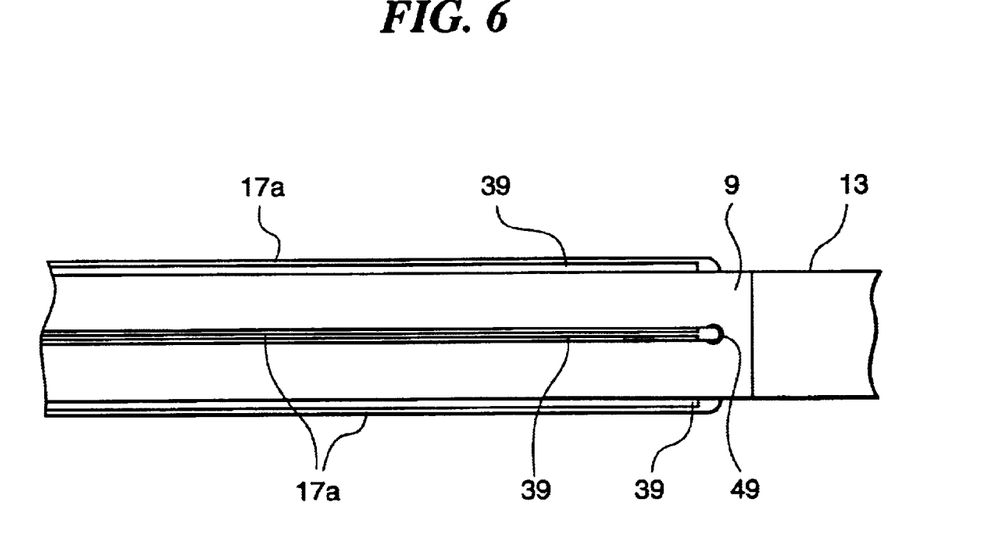
FIG. 6 is a drawing showing a side view of a portion around the distal end of the flexible section of the insertion tube of the colonoscope according to the invention.

FIG. 6 is a drawing showing a side view of a portion around the distal end of the flexible section of the insertion tube of the colonoscope according to the invention.

At the distal section 11 of the insertion tube 9, as shown in FIG. 5, an image receiving window 19, one or two light projecting windows 21, a suction and forceps opening 23, and an air-water nozzle 25 are provided. The image-receiving window 19, equipped with an objective lens when the observation device is a fiber scope, or an image pick-up device, such as a CCD, when it is an electronic scope, receives an image from the distal end surface thereof. The received image is transmitted to the operation unit 7 by an image guide of the fiber scope or lead wire of the electronic scope, which is inserted in the insertion tube 9, and then transmitted through a universal cord 27 to a display and the like to be displayed. A light guide, such as an optical fiber, is inserted in the bore of each of the light projecting windows 21, runs through the operation unit 7 and is connected to a light source outside via the universal cord 27. The light source projects light from the distal end surface of the light guide.

The suction and forceps opening 23 is connected to a forceps insertion opening 29 of the operation unit 7 and a forceps 31 is inserted therein. The tip ends of the forceps 31, protruding from the distal end of the insertion tube 9, are manipulated at the proximal part of the forceps 31 to perform procedures such as to treat a lesion of a patient or to collect a tissue from a patient.

The bore of the air-water nozzle 25 is a water-air supply channel, and air or a cleaning solution is injected through the air-water nozzle 25 by manipulating the air-water supply button 33 of the operation unit 7. Through the suction and forceps opening 23, body fluid or cleaning solution remaining in the colon is sucked out and discharged outside of the patient's body. This operation is carried out by manipulating a suction control button 35 of the operation unit 7.

The bending section 13 of the insertion tube 9 is able to bend upwardly and downwardly, to right and left, and obliquely by manipulating a control latch 37 provided at the operation unit 7.

A plurality of endless belts 17 are longitudinally arranged on the outside surface of the flexible section 15 of the insertion tube 9. The diameter of the flexible section 15 is preferably 5 to 30 mm; 16 mm is most preferable. A larger number of endless belts 10 is preferable, because the larger the number of endless belts, the higher the self-propelling ability of the colonoscope. As shown in FIG. 4, the outside portion 17a of the endless belt 17 is supported by a guide hook 39 provided at the outside surface of the insertion tube 9. The inside portion 17b of the endless belt 17 passes through a guide pipe 41 in the flexible section. Each of the guide hooks 39, having a circular-arc-shaped cross section whose interior angle thereof is over 180 degrees, is longitudinally mounted at the flexible section 15 so that a portion of each of the endless belts 17 exposed from each of the guide hooks 39 will be positioned radially and outwardly (as shown in FIG. 6). Accordingly, the outer surfaces of the endless belts 17 supported by the guide hooks 39 are exposed to the outside of the guide hooks 39 so that the endless belts can maintain a sufficient contact area with the inner wall of the colon when inserted into the colon. Even when the flexible section 15 is severely bent, the endless belts 17 will not come off the guide hooks 39.

Each of the endless belts 17 is made of a flexible and strong material such as, for instance, carbon fiber or resin, and, as shown in FIGS. 3(A), (C), is provided with an axial belt 18a and a plurality of rack gear teeth 18b arranged along the length of the axial belt 18a. The axial belt 18a has a vertical circular cross section to the longitudinal direction and a diameter of 1 to 3 mm. The rackgear teeth 18b also have a vertical circular cross section to the longitudinal direction, and are separately arranged at a constant distance on the outside surface of the axial belt 18a on the same axis as that of the axial belt 18a. The rack gear teeth 18b have a diameter of 1 to 3 mm and a thickness of 0.1 to 1.0 mm, and the distance between any two teeth of the rack gear teeth 18b is 0.1 to 1.0 mm. The outside surface of the rack gear teeth 18b may be coated with a high frictional material. The outside surface of the pulley 43c including the pinion gear teeth 43c, as described hereinafter, may also be coated with a high frictional material. The length of the endless belt is described later.

When cleaning the colonoscope, it is necessary to remove the endless belt 17 from the insertion tube 9, so that it is capable of one-way separation and reconnection.

The endless belt has a circular cross section so as to be able to bend in all radial directions to the axis thereof with equal force. So, when the insertion tube is inserted along the bending of the colon, the endless belt can easily follow the movement of the insertion tube. Since the rack gear teeth are formed on the outer surface of the endless belt, if the endless belt should twist, a part of the rack gear teeth will contact the wall of the colon and enable the endless belt to be rubbed against the wall of the colon. Accordingly, the friction force between the endless belt and the wall of the colon will be increased thereby improving the self-propelling ability.

Next, referring now to FIG. 2, the construction of the proximal part of the guide pipe 41 and the driving unit 5 of the endless belt will be explained.

The proximal part of the guide pipe 41 is connected to a guide pipe opening 45 provided at the side surface of the driving unit casing 3. The driving unit casing 3 is larger than the insertion tube 9 in diameter. The guide pipe 41 comprises an inclined section 41a, extending diagonally from the guide pipe opening 45 to the insertion tube 9, and a guide section 41c, which extends straight in the insertion tube 9, running from the inclined section 41a to a bending section 41b.

The drive roller 43, pinching the endless belt 17, is mounted outside of the proximal end of the guide pipe 41 in the driving unit casing 3. The endless belt 17 penetrates the sidewall of the guide pipe 41 at the inclined section 41a of the guide pipe 41. That is, the exterior portion 17a of the endless belt 17 runs from the outside surface of the insertion tube 9 into the guide section 47, then extends toward the proximal end crossing holes formed at the two side walls of the inclined section 41a and is wound up and held by the drive roller 43. On the other hand, the interior portion 17b of the endless belt 17 penetrates the side wall of the guide pipe 41 at the inside of the inclined section 41a and runs into the guide pipe 41, and, via the inside of the pipe 41, to a guide hole 49 (as shown in FIG. 6) provided near the distal end of the flexible section 15 of the insertion tube 9.

The guide hole 49, as shown in FIG. 6, is preferably positioned at 0 to 10 cm from the distal end of the flexible section 15. This is because the greater the surface where the inside wall of the colon is in contact with the outside portion 17a of the endless belt 17, the higher the self-propelling ability of the self-propelled colonoscope.

On the other hand, the distal section of the insertion tube 9, inserted into the colon, advances from the sigmoid colon to the ileum, and through the descending colon, the transverse colon and the ascending colon, as mentioned above. The diameter of the flexible section is about 16 mm. When the distal end of the colonoscope advances into the colon while bending, the inner ring length and the outer ring length of the inserted flexible section 15 differ due to the bending of the colon. When the distal end of the insertion tube reaches the ileum, and the flexible section 15 with a diameter of 16 mm turns around 360 degrees, the outer circle length is 3.12% longer than the straight length.

Accordingly, it is necessary to set the length of the endless belt 17, arranged on the surface of the flexible section 15, to allow for differences between the inner ring length and the outer ring length. For this reason, the length of the endless belt is made to be 102 to 104% of the length of such belt when it tightly turns around from the guide hole near the tip of the flexible section 15 to the same guide hole 49 through the driving unit, while the flexible section 15 is kept straight. Since the length of the endless belt 17 is set as above, the endless belt 17 can sufficiently follow the bending of the flexible section 15. Therefore, it is possible to make the colonoscope advance into the colon stably.

The drive roller 43 comprises a pulley 43b on which the endless belt 17 is wound, and a bevel gear 43a, connected to the same shaft as the pulley 43b. On the side surface of the pulley 43b, a recess having a semi-circular cross section is formed, as shown in FIG. 3(C). In the recess, the pinion gear teeth 43c are formed, which are engaged with the rack gear teeth 18b of the endless belt 17.

As mentioned above, the endless belt has a length which exhibits a certain allowance. The pinion gear teeth 43c are formed on the side surface of the pulley 43b and drive the endless belt 17. The endless belt 17 and the pulley 43b engage with the rack gear teeth 18b and the pinion gear teeth 43c so that the endless belt can be driven without idling.

As shown in FIG. 2, a bevel gear 50 is engaged with the bevel gear 43a, and is arranged perpendicularly to the bevel gear 43a. A spur gear 53 is fixed to the proximal part of a gear shaft 51 of the bevel gear 50. The spur gear 53 is engaged with a large spur gear 59 fixed to a motor shaft 57 of a motor 55. Consequently, when the motor shaft 57 revolves by driving the motor 55, the bevel gear 43a will revolve, via the large spur gear 59, the spur gear 53, and the bevel gear 50, and accordingly the pulley 43b will revolve together.

On the circumference of the large spur gear 59, the same number of drive rollers 43, bevel gears 50, gear shafts 51, and spur gears 53, as endless belts 17, are mounted. Incidentally, at that time, a gear 63 may be mounted between the large spur gear 59 and the spur gear 53 in order to drive each of the endless belts 17 in the same direction.

The motor 55, the large spur gear 59, the spur gear 53, the gear shaft 51, the bevel gear 50, and the drive roller 43 are mounted in the driving unit casing 31 provided at the proximal end side of the guide pipe opening 45. On the side surface of the driving unit casing 3, a cleaning opening 60 is formed. The opening 60 is provided with a lid 61, shown in FIG. 1, and can be opened or closed. The opening 60 may be opened to access the space containing the large spur gear 59, the spur gear 53, the gear shaft 51, the bevel gear 50, and the drive roller 43. A space containing the large spur gear 59, the spur gear 53, the gear shaft 51, the bevel gear 50, and the drive roller 43, and a space provided with the motor 55 are water-tightly isolated.

When the motor 55 is driven to rotate the pulley 43b counterclockwise, the exterior portion of endless belt 17 engaged with the pulley 43b will rotate to the left. At this time, if the outer surface of the endless belt 17 is in contact with the inside wall of the colon, the insertion tube 9 will be fed forward to the right as illustrated in FIG. 2 by friction between the endless belt 17 and the inside wall of the colon. The insertion tube 9 moves back by rotating the motor 55 clockwise.

The present invention can provide a self-propelled colonoscope improved in the bending ability and the self-propelling ability.

What is claimed is:

1. In a self-propelled colonoscope insertable into a colon of a patient by driving endless belts arranged on the outside of a flexible section of an insertion tube, the improvement wherein:

each endless belt has a substantially circular cross section;

rack gear teeth having a circular cross section are formed on the outside of said endless belt; and a recess having a semi-circular cross section and pinion gear teeth which correspond to the shape of said endless belt and said rack gear teeth are formed on the outside of a pulley for driving said endless belt.

2. The self-propelled colonoscope according to claim 1, wherein the outside surface of said pulley for driving said endless belt and the outside surface of the endless belt are coated with high frictional material.

* * * * *